United States Patent
Jonsson et al.

(10) Patent No.: US 9,753,010 B2
(45) Date of Patent: Sep. 5, 2017

(54) TWO-DIMENSIONAL GEL ELECTROPHORESIS APPARATUS AND METHOD

(71) Applicant: Biocule (Scotland) Limited, Roslin (GB)

(72) Inventors: Jon Johannes Jonsson, Reykjavik (IS); Gudmundur Heidar Gunnarsson, Hofn (IS); Bjarki Gudmundsson, Hafnarfjordur (IS); Hans Guttormur Thormar, Reykjavik (IS); Kristjan Leosson, Reykjavik (IS); Jacinto Peter Estibeiro, Duns (GB)

(73) Assignee: BIOCULE (SCOTLAND) LIMITED, Roslin (GB)

( * ) Notice: Subject to any disclaimer, the term of this patent is extended or adjusted under 35 U.S.C. 154(b) by 76 days.

(21) Appl. No.: 14/971,216

(22) Filed: Dec. 16, 2015

(65) Prior Publication Data
US 2016/0178575 A1    Jun. 23, 2016

Related U.S. Application Data

(63) Continuation of application No. 13/984,616, filed as application No. PCT/GB2012/050295 on Feb. 10, 2012, now abandoned.

(30) Foreign Application Priority Data

Feb. 10, 2011 (GB) .................................. 1102385.0

(51) Int. Cl.
G01N 27/447    (2006.01)
B01D 57/02    (2006.01)

(52) U.S. Cl.
CPC ....... *G01N 27/44778* (2013.01); *B01D 57/02* (2013.01); *G01N 27/44713* (2013.01)

(58) Field of Classification Search
CPC ....... G01N 27/44773; G01N 27/44778; G01N 27/44713
See application file for complete search history.

(56) References Cited

U.S. PATENT DOCUMENTS

| 4,148,703 A | * | 4/1979 | Trop ........................ C12N 9/00 204/457 |
| 4,861,448 A | | 8/1989 | Cantor et al. |

(Continued)

FOREIGN PATENT DOCUMENTS

| AU | 2004200643 | 3/2004 |
| CA | 2 327 527 | 6/2002 |

(Continued)

OTHER PUBLICATIONS

Chu, et al., "Separation of Large DNA Molecule by Contour-Clamped Homogenous Electric Fields," SCIENCE 243, No. 4783, pp. 1582-1585 (1986).

*Primary Examiner* — Alexander Noguerola
(74) *Attorney, Agent, or Firm* — Fay Sharpe LLP

(57) ABSTRACT

Two-dimensional gel electrophoresis apparatus includes an electrophoresis zone having four edges defined by a plurality of electrodes. A pair of opposed edges are defined by groups of discrete electrodes. Discrete electrodes within each group are electrically isolated from each other while the other pair of opposed edges are used to generate an electrical field. As a result, the electrical field is less distorted than would be the case if each edge was defined by a single elongate electrode. The apparatus can be provided as a cassette with electrodes configured to guide gas generated during electrolysis out of the cassette through apertures, to reduce the build up of combustible gases.

17 Claims, 7 Drawing Sheets

(56) References Cited

U.S. PATENT DOCUMENTS

| | | |
|---|---|---|
| 4,874,491 A | 10/1989 | Stalberg |
| 4,892,639 A | 1/1990 | Sarrine et al. |
| 4,911,817 A | 3/1990 | Kindlmann et al. |
| 5,045,164 A | 9/1991 | Tansamrit et al. |
| 5,084,157 A | 1/1992 | Clark et al. |
| 5,209,831 A | 5/1993 | MacConnell |
| 5,405,519 A | 4/1995 | Schwartz |
| 5,549,796 A | 8/1996 | Chu et al. |
| 5,582,702 A | 12/1996 | Cabilly et al. |
| 5,702,898 A | 12/1997 | Bonaldo et al. |
| 5,865,974 A | 2/1999 | Cabilly et al. |
| 6,165,337 A | 12/2000 | Stio |
| 6,368,481 B1 | 4/2002 | Sowa et al. |
| 6,379,516 B1 | 4/2002 | Cabilly et al. |
| 6,379,517 B1 | 4/2002 | Heydecke et al. |
| 6,562,213 B1 | 5/2003 | Cabilly et al. |
| 6,682,641 B1 | 1/2004 | Finney et al. |
| 2002/0106666 A1 | 8/2002 | Hayashizaki |
| 2003/0148286 A1 | 8/2003 | Larose et al. |
| 2004/0231991 A1 | 11/2004 | Herrera Isidron et al. |
| 2004/0256233 A1 | 12/2004 | Yonish |
| 2006/0057575 A1 | 3/2006 | Jonsson et al. |
| 2006/0163067 A1 | 7/2006 | Sevigny et al. |
| 2006/0228721 A1 | 10/2006 | Leamon et al. |
| 2008/0318233 A1 | 12/2008 | Glenn et al. |
| 2009/0107841 A1 | 4/2009 | Gunnarsson et al. |

FOREIGN PATENT DOCUMENTS

| | | |
|---|---|---|
| CA | 2 390 426 | 7/2002 |
| CA | 2 604 095 | 10/2006 |
| EP | 0307332 | 3/1989 |
| EP | 0824689 | 2/1998 |
| EP | 1379864 | 1/2004 |
| EP | 1442156 | 8/2004 |
| EP | 1804058 | 7/2007 |
| EP | 1791955 | 2/2011 |
| EP | 1537412 | 1/2013 |
| GB | 2276008 | 9/1994 |
| JP | 2005-062075 | 3/2005 |
| WO | WO 00/72182 | 11/2000 |
| WO | WO 00/77510 | 12/2000 |
| WO | WO 01/77658 | 10/2001 |
| WO | WO 01/98538 | 12/2001 |
| WO | WO 02/18655 | 3/2002 |
| WO | WO 02/45472 | 6/2002 |
| WO | WO 02/084273 | 10/2002 |
| WO | WO 02/95072 | 11/2002 |
| WO | WO 03/029523 | 4/2003 |
| WO | WO 2006/025074 | 3/2006 |

* cited by examiner

TWO-DIMENSIONAL GEL ELECTROPHORESIS APPARATUS AND METHOD

This application is a continuation of U.S. application Ser. No. 13/984,616, filed Aug. 9, 2013, claims priority to and the benefit of PCT International Application Number PCT/GB2012/050295, filed on Feb. 10, 2012, and GB 1102385.0 filed Feb. 10, 2011, the disclosures of which are incorporated herein by reference in their entireties.

FIELD OF THE INVENTION

The invention concerns apparatus and a method for separating a mixture of molecules using two-dimensional gel electrophoresis.

BACKGROUND TO THE INVENTION

The separation of biologically active or important molecules is a key area for biochemistry and molecular biology. One standard method for isolating or identifying such molecules is polyacrylamide-gel electrophoresis (PAGE), for example, where the molecules in question are induced to migrate through a polyacrylamide-gel matrix by an electric field. For a given magnitude of the electric field, the speed at which the molecules migrate is dependent on their mass, charge and conformation where the smaller molecules, or molecules with a high charge/mass ratio migrate at a faster rate than the larger molecules or molecules with a lower charge/mass ratio. After staining of the resultant gel with an appropriate agent able to stain the target molecules, a distribution of bands is revealed in order of molecular mass. Use of molecular markers (a mixture of standard molecules whose masses are known) running in parallel to the sample to be identified or separated allows the molecular masses to be accurately assessed.

Electrophoresis can be performed to separate molecules by properties other than their mass by appropriate treatment of the gel matrix. For example, molecules can be separated by isoelectric focussing, whereby a pH gradient is formed across the gel matrix prior to electrophoresis and molecules are drawn to the point on the gradient where their overall charge is zero (otherwise known as their isoelectric point).

In order to better separate molecules within a sample, it is known to carry out two-dimensional electrophoresis in which a sample is subjected first to an electric field in a first direction and then a second direction. Either the electrophoresis gel will have a property which varies parallel to the first or second direction (e.g. pH) or a treatment will be applied to molecules within the sample, for example a treatment which denatures molecules within the sample, between electrophoresis in the first direction and electrophoresis in the second direction. For example, in order to analyse the composition of a mixture of RNA and DNA molecules of a range of lengths and potentially including both single- and double-stranded molecules, a sample may be separated by electrophoresis in a first dimension, and then denatured to separate double-stranded molecules, and then separated by electrophoresis in a second dimension.

One known way of carrying out two-dimensional gel electrophoresis is to provide a single pair of spaced apart electrodes which are positioned on opposing sides of a region of an electrophoresis gel. Electrophoresis is then carried out in a first direction. After an electrophoresis process, the gel is rotated relative to the electrodes enabling electrophoresis to then be carried out in a second direction. This process does, however, require manual intervention or complex automation. Accordingly, it has been proposed to provide two-dimensional gel electrophoresis apparatus having two sets of opposed electrodes in situ for carrying out electrophoresis in a first direction (between a first set of opposed electrodes) and then in a second direction (between the other set of opposed electrodes). For example, US 2009/0107841 (Gunnarsson et al.) discloses gel electrophoresis apparatus having two sets of electrodes, arranged such that two electric fields normal to each other can be alternatively applied to the gel without a requirement for the gel to be rotated in between. Gel can be provided in a cassette form enabling rapid separation of mixtures of molecules.

However, in known two-dimensional gel electrophoresis apparatus with two sets of opposed electrodes, each set of opposed electrodes comprises a single elongate electrode extending along one edge of the zone within which electrophoresis can occur. A problem with this arrangement is that because the electrodes are conductors which must remain at substantially the same electrical potential along their entire length, the pair of electrodes which are not in use distort the electrical field generated by a pair of electrodes which are in use, distorting the distribution of sample molecules after electrophoresis and reducing the surface area within which two-dimensional gel electrophoresis can be effectively carried out.

Therefore, some aspects of the current invention aim to provide a two-dimensional gel electrophoresis system in which a more uniform electric field can be produced across the electrophoresis gel in both dimensions to provide a more even distribution of separated molecules and to maximise the useful area of the electrophoresis gel.

SUMMARY OF THE INVENTION

According to a first aspect of the invention there is provided two-dimensional gel electrophoresis apparatus comprising: a plurality of electrodes defining an electrophoresis zone and a gel support for retaining an electrophoresis gel in the electrophoresis zone, the electrophoresis zone having at least four edges, each of which is defined by at least one of the said plurality of electrodes, the at least four edges comprising first and second pairs of opposed edges, wherein at least one of the second pair of edges is defined by a group of discrete electrodes.

The invention extends in a second aspect to electrophoresis apparatus according to the first aspect of the invention further comprising electrophoresis gel retained in the electrophoresis zone by the gel support. The electrophoresis apparatus may take the form of a cassette having a body which comprises the gel support and retains electrophoresis gel within the electrophoresis zone.

The invention also extends in a third aspect of the invention to a method of carrying out two-dimensional gel electrophoresis comprising the steps of: providing a plurality of electrodes which define an electrophoresis zone and providing electrophoresis gel in the electrophoresis zone, the electrophoresis zone having at least four edges, each edge defined by at least one of the said plurality of electrodes, the at least four edges comprising first and second pairs of opposed edges, wherein at least one of the second pair of edges is defined by a group of discrete electrodes; and applying a potential difference between the electrodes defining the first pair of opposed edges, to generate an electrical field in a first direction across the electrophoresis zone, whilst the electrodes within the or each group of discrete electrodes which define the at least one of the second pair of edges are electrically isolated from each other.

Typically, each of the second pairs of edges are defined by a group of discrete electrodes. Typically, the electrodes within the groups of discrete electrodes which define each of the second pairs of edges are electrically isolated from each other whilst a potential difference is applied between the electrodes defining the first pair of edges to generate an electrical field across the electrophoresis zone.

By defining the at least one (and typically both) of the second pair of edges using a group of discrete electrodes and carrying out electrophoresis by applying a potential difference to the electrodes defining the first pair of opposed edges to generate an electrical field across the electrophoresis zone whilst at least two (and typically each) of the electrodes within the (or typically each) group of discrete electrodes which define at least one (and typically both) of the second pair of opposed edges are electrically isolated from each other, distortion of the electrical field generated in the first direction by the electrodes defining the second pair of opposed edges is reduced. This contrasts with known electrophoresis apparatus in which each of the second pair of edges is defined by a single elongate electrode, short circuiting the electric field generated by the electrodes, defining the first pair of edges, and bending electrical field lines.

Thus, a more uniform electrical field can be generated in the first direction, providing a more controlled and precisely defined separation of molecules. Furthermore, a larger portion of the electrophoresis zone defined by the electrodes may be used.

Preferably, at least one (and typically both) of the first pair of edges is defined by a group of discrete electrodes. In this case, the method typically comprises the step of applying a potential difference between the electrodes defining the second pair of opposed edges, to generate an electrical field in a second direction across the electrophoresis zone, whilst at least two (and typically each) electrode within the (or typically each) group of discrete electrodes which define the at least one (and typically both) of the first pair of edges are electrically isolated from each other.

The first and second directions are at an angle to each other. However, the first and second directions are typically orthogonal to each other. In this case, the electrophoresis zone is typically rectangular, for example square or oblong.

The method typically comprises the step of treating the sample within the electrophoresis zone after the application of an electrical field in the first direction and before the application of an electrical field in the second direction, so that molecules within the sample respond differently to the electrical field in the second direction. Gel within the electrophoresis zone may comprise an activatable denaturing agent. The activatable denaturing agent may be operable to separate double stranded nucleic acid molecules, or a mixture of proteins. The activatable denaturing agent may be temperature activatable, for example, the activatable denaturing agent may be urea. Thus, the treatment may be heating. However, the activatable denaturing agent may be activatable by another means, for example light.

Preferably, the discrete electrodes within the or each group of discrete electrodes are electrically isolatable from one another. Typically each of the plurality of electrodes within a group has a respective electrical contact, in direct electrical communication with only one said electrode, for connection to isolating means thereby enabling the electrodes within each group to be isolatable from each other or connectable to each other by way of isolating means.

Preferably, the isolating means is operable in an isolating mode, in which discrete electrodes within a group are isolated, and in an operational mode, in which the discrete electrodes within a group are electrically connected to one or more electrical terminals.

Isolating means may be provided externally to the electrophoresis apparatus. For example, the electrophoresis apparatus may be a cassette having a separate electrical contact associated with each electrode and in direct electrical communication with only one said electrode. Some or all said electrical contacts may be a surface of an electrode. During use, the electrical contacts may be in electrical communication with external electrical circuits associated with each group of discrete electrodes. Said electrical circuits may comprise isolating means for each electrode within the groups of discrete electrodes.

Alternatively, the electrophoresis apparatus may comprise isolating means. For example, the electrophoresis apparatus may comprise an electrical terminal for connection to a pole of a power supply in direct electrical communication with all electrodes within each individual group of discrete electrodes, and isolating means between said electrical terminal and individual electrodes within each group of discrete electrodes.

The isolating means may comprise an electrical circuit extending between the electrodes in a group of discrete electrodes and an electrical terminal, the electrical circuit operable between an isolating mode and an operational mode. A said electrical circuit is typically provided for each group of discrete electrodes.

Typically, in the isolating mode the electrodes in the group are typically substantially electrically isolated from each other and from any electrical terminal. In the operational mode the electrodes in the group are electrically connected to an electrical terminal. Several or all of the electrodes may in that case be connected to the same electrical terminal. Each electrode in the group may adopt the same potential in the operational mode, for example, each electrode in the group may be in direct electrical communication in the operational mode. However, it may be that the electrical circuit associated with the group of electrodes determines that at least two of the electrodes within the group of electrodes have different potentials in use. The electrical circuit may be selected to determine the relative potentials of each electrode in the group in the operational mode to apply a uniform electric field to the electrophoresis zone.

The isolating means typically comprises one or more switches, for example one or more relays or solid state switches. The method may comprise controlling one or more switches to electrically isolate electrodes within a group of discrete electrodes from each other.

The electrical terminal may be a connection to an internal power supply, such as a battery, but is typically a connection to an external power supply. The electrical circuit may be adapted to switch from the isolating mode to the operational mode when a potential difference is applied between two electrical terminals, each of which is for providing an electrical potential to opposed groups of discrete electrodes.

The electrophoresis apparatus may be connectable to an external power supply and external isolating means. For example, the electrophoresis apparatus may comprise a cassette having a separate electrical terminal in electric communication with each electrode, or a separate aperture for receiving an external electrical terminal, such as a connecting pin, to form an electrical connection with each electrode.

The gel support may comprise a body defining a gel retaining volume therein. The electrophoresis apparatus may be in the form of a cassette having a body defining a gel retaining volume therein. The gel support may comprise a tray defining a gel retaining volume. Electrophoresis gel may be provided within the gel retaining volume.

Typically, the gel support comprises a gel supporting sheet. Electrophoresis gel is typically retained as a sheet on the gel supporting sheet. The gel support may further comprise a facing sheet such that electrophoresis gel may be retained between the gel supporting sheet and the facing sheet. The gel supporting sheet is typically planar. The facing sheet is typically planar.

The electrodes may be formed on a gel facing surface of the gel support, for example, on the gel facing surface of the gel supporting sheet. The electrodes may be electrodes formed by printing. The electrodes, or groups of discrete electrodes, typically comprise carbon epoxy, but may, for example, comprise silver epoxy or silver paste, platinum paste or another metal or conducting oxide. The facing sheet may comprise access ports having electrical conductors extending therethrough for providing electrical connections to the electrodes.

The gel support may further comprise an insulating spacer around the periphery of the gel support such that at least part of the discrete electrodes extend into or beneath the insulating spacer.

The gel support may comprise one or more apertures to enable gas produced during electrophoresis to egress from the gel support. Where the gel support encloses the electrophoresis gel, the one or more apertures preferably enable gas produced during electrophoresis to egress from the electrophoresis apparatus.

For example, the gel support may comprise one or more apertures, each of which is associated with a said electrode, to enable gas produced by the respective electrode to egress from the gel support. The gel supporting sheet or, more typically, the facing sheet, may comprise one or more said apertures. This is a significant safety feature, minimising the build up of hydrogen and oxygen.

Some or all of the electrodes may comprise a gas guiding formation operable to direct generated gas towards a said aperture. For example, the electrodes may have an outer wall having a concave indentation and the respective aperture may be located adjacent to the concave indentation so that a portion of the outer wall forming the concave indentation functions as a gas guiding formation.

Some or all of the electrodes may have an outer wall with a concave formation on the side facing the opposed edge of the electrophoresis zone. Thus, some or all of the electrodes may have a plurality of lobes on the side facing the opposed edge of the electrophoresis zone. This provides a more even electrical field and reduces the risk of electrode burning.

Preferably, some or all of the electrodes comprise a smooth continuous surface such that there are no sharp corners or vertices to further reduce the risk of electrode burning.

Preferably, discrete electrodes in a group of discrete electrodes are arranged in a line defining part of an edge of the electrophoresis zone. Preferably, the ratio of the discrete electrode width parallel to the respective edge (w) to the sum of said width and the space (s) between discrete electrodes, $$r = \frac{w}{w+s}$$ (Equation 1)

is between 0.3 and 0.7. More preferably, the width of each of the discrete electrodes, parallel to the respective edge, is substantially the same as the spacing between discrete electrodes ($r=0.5$). We have found that this gives a good surface area of uniform electrical field while avoiding excessive electrical current density in the individual electrodes.

The current supplied to individual discrete electrodes may be regulated by a current regulator such that the current at any one discrete electrode is maintained within predetermined bounds to prevent the discrete electrodes short circuiting.

Each group of discrete electrodes preferably comprises three or more discrete electrodes. The opposed groups of discrete electrodes defining the second pair of edges preferably each comprise four or more discrete electrodes. The provision of a relatively large number of electrodes enables relatively even electrical fields to be generated.

The electrophoresis gel may be polyacrylamide with the common buffer Tris Borate Ethylenediaminetetraacetic acid, or EDTA (TBE) but may be other gel matrices and buffers used in electrophoresis such as agarose and Tris Acetate EDTA (TAE). Electrophoresis gel may be pre-cast within the gel support, for example when the electrophoresis apparatus is provided as a cassette. Alternatively, electrophoresis gel may be cast within the gel support just prior to use, or a pre-cast gel placed within the gel support prior to use.

Preferably, the apparatus does not comprise an external buffer reservoir, as normally required in conventional gel electrophoresis.

The electrophoresis gel may comprise a temperature activated denaturing agent, such as urea. The electrophoresis gel may further comprise a labelling agent operable to label sample molecules introduced to the electrophoresis gel such that after electrophoresis the sample molecule are detectable, for example visually observable. The labelling agent is typically a fluorescent species such as Ribo Green, SYBR Green or LC Green, but may be a non-fluorescent dye or a radioactive species.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
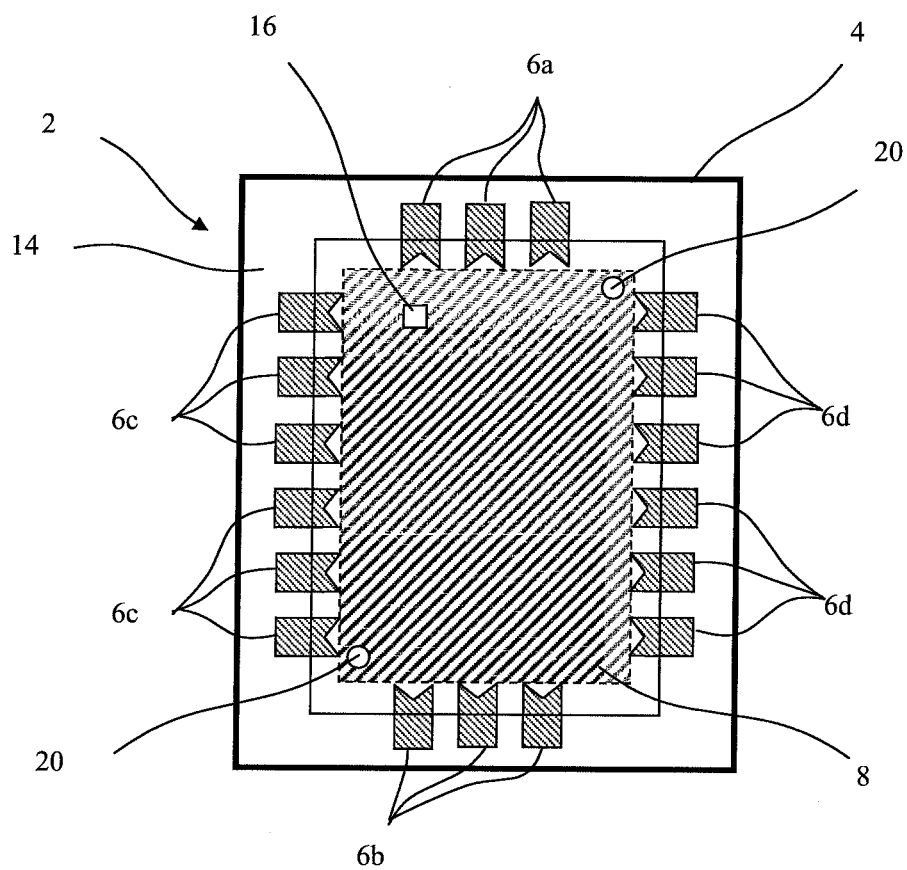
FIG. 1 is a plan view of a two-dimensional gel electrophoresis cassette.

With reference to FIGS. 1 to 4, 5A, 5B, 6A and 6B, there is provided two-dimensional electrophoresis apparatus comprising a cassette 2 having a body 4 functioning as the gel support. The gel support retains a gel matrix formed of electrophoresis gel. The cassette includes four groups of discrete electrodes 6a, 6b, 6c, 6d, which are formed around the edges of and define an electrophoresis zone 8, within which electrical fields can be created between opposed groups of discrete electrodes to carry out electrophoresis.

Each of the four groups of discrete electrodes comprises a plurality of discrete electrodes. A first set of electrodes 6a, 6b, defining a first pair of opposed edges of the electrophoresis zone is used to generate an electrical field in a first direction and a second set of electrodes 6c, 6d, defining a second pair of opposed edges of the electrophoresis zone, is used to generate an electrical field in a second direction, orthogonal to the first direction.

Figure 2:
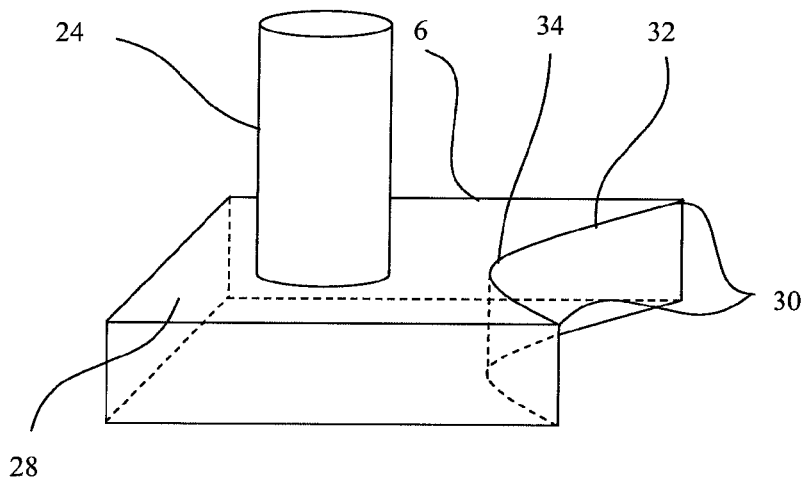
FIG. 2 is a perspective view of a single discrete electrode.
Figure 3:
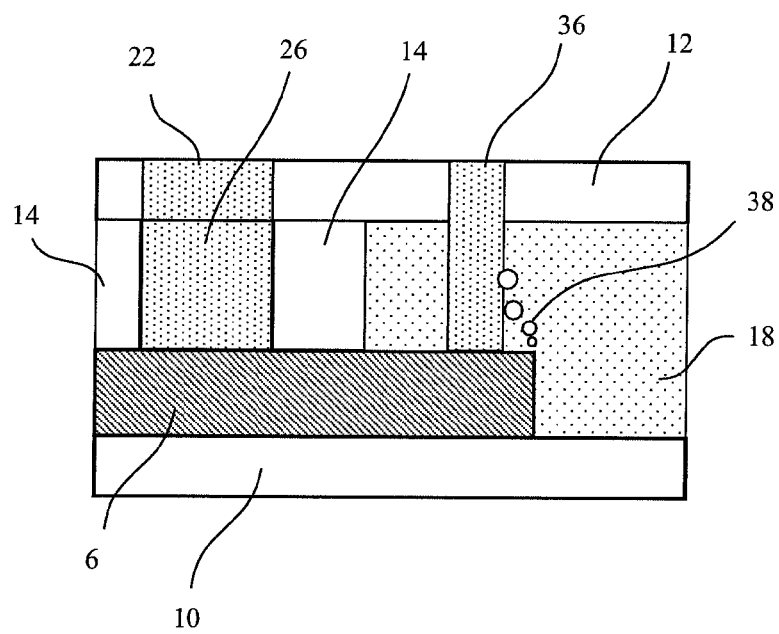
FIG. 3 is a side view of a discrete electrode in situ within the gel support.
Figure 4:
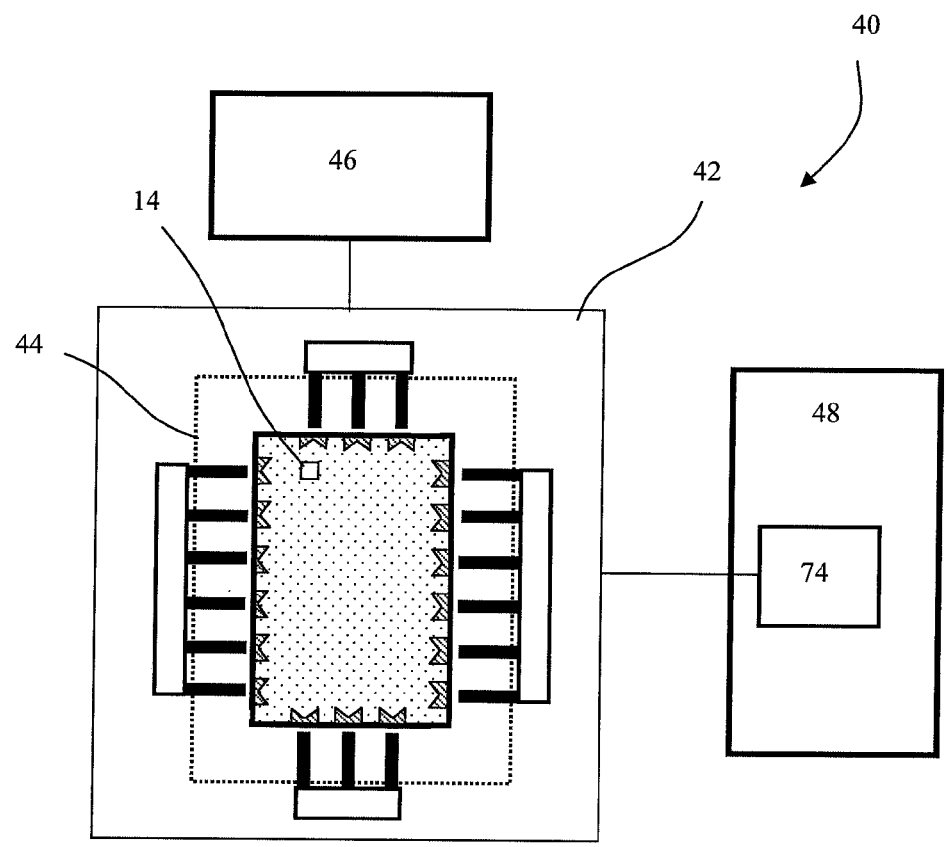
FIG. 4 is a plan view of a two-dimensional gel electrophoresis cassette mounted on an interface unit.
Figure 5A:
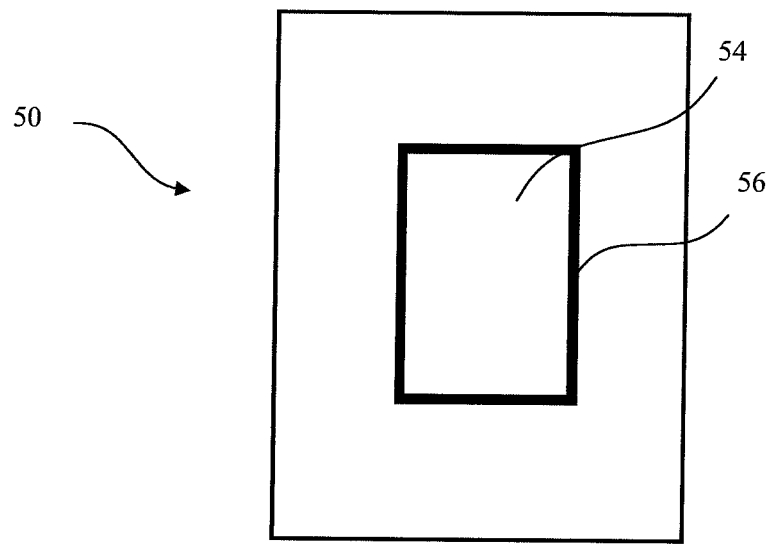
FIG. 5A is a plan view of an electrical interface unit base.
Figure 5B:
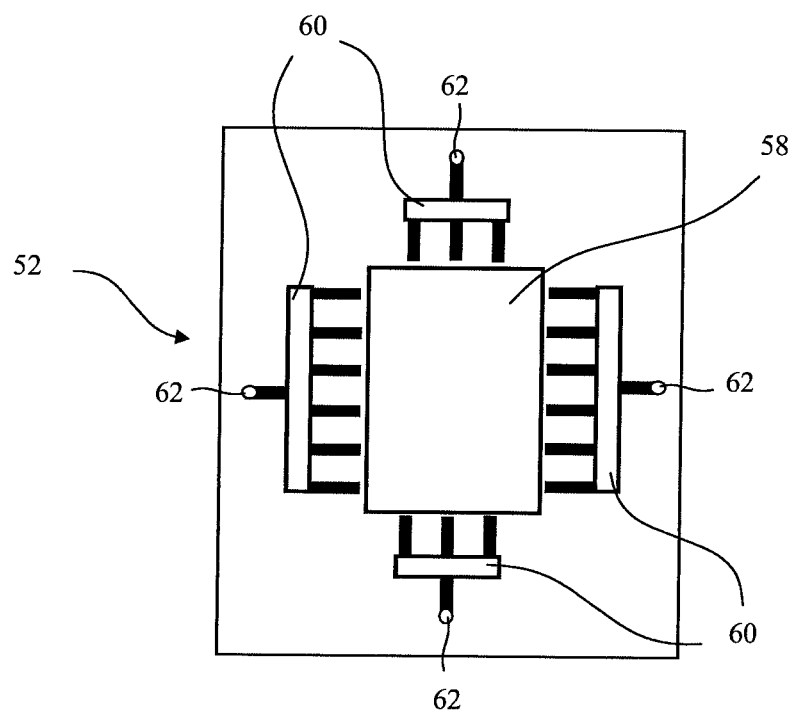
FIG. 5B is a plan view of a detachable lid.

With references to FIGS. 2 and 3, the gel support comprises a gel supporting sheet 10 and a facing sheet 12, which are opposed and which together retain gel matrix. Substantially enclosing the electrophoresis gel facilitates polymerisation and reduces evaporation. The gel supporting sheet may be underneath the gel in use, although in some embodiments the gel may be oriented vertically in use and the gel supporting sheet and facing sheet may each provide equivalent support to gel matrix. The gel support further includes an electrically insulating spacer 14 around the periphery of the gel support. Part of each of the discrete electrodes extends between the electrically insulating spacer and the gel supporting sheet.

The facing sheet comprises a sample loading aperture 16, through which a sample can be introduced to a gel matrix 18 retained by the gel support within the electrophoresis zone. The gel matrix extends beyond the electrophoresis zone such that the discrete electrode elements are in electrical contact with the ions within the gel matrix. The facing sheet also includes two pouring apertures 20 which are provided to enable gel matrix to be poured into the gel support. In this example, the gel matrix will typically be preloaded into the cassette, in which case the pouring apertures will have been used during manufacture although, in alternative embodiments, apparatus may be provided without gel matrix present, in which case the pouring apertures are employed to enable gel matrix to be loaded. In further alternative embodiments, a cassette may have been preformed without pouring apertures by providing an open gel support which is subsequently sealed during manufacture.

Each electrode (one of which is shown generally as 6 in FIGS. 2 and 3) is formed on the gel supporting sheet by the printing of carbon epoxy. The facing sheet includes access ports 22 to enable electrodes within the cassette to be individually connected in use to an electrical circuit by way of metal connecting pins 24 extending from an interface unit, described below. The ports connect with bores 26 through the electrically insulating spacer to electrically insulate metal connecting pins from the gel matrix within the cassette.

Each electrode has a smooth continuous outer surface 28 extending around the electrode. The electrode has two lobes 30 facing towards the opposed electrodes across the electrophoresis zone. Between the lobes, the outer surface includes a concave indentation 32 having a midpoint 34. The facing sheet includes an aperture 36 adjacent each electrode and overlapping with the said midpoint of the concave indentation.

This configuration has two purposes. Firstly, the bilobal shape of the electrodes enables the generation of a regular electrical field. Secondly, the outer surface of the electrode which forms the concave indentation acts as a gas guiding formation, guiding gas bubbles 38, which are formed during use, to the midpoint of the concave indentation, adjacent the respective aperture. Thus, a path is provided for hydrogen and oxygen formed during electrolysis to egress from the cassette.

The electrodes are typically spaced apart equally and the separation between electrodes is substantially the same as the width of the electrodes. We have found that this gives a good surface area of uniform electrical field.

The current supplied to each discrete electrode is typically regulated by a current regulator to maintain the current within predetermined bounds. Such regulation has been found to prevent the current at any single discrete electrode from becoming too high such that short circuits may arise.

The dimensions of the cassette will be selected depending on the intended application of the apparatus but may, for example, be 66×90×4.5 mm with a gel thickness of 2.5 mm.

The cassette is mounted in use within an interface unit 40, which comprises a support block 42, a temperature regulation plate 44, a power supply 46 and a control unit 48. The support block has a base 50 and a detachable lid 52. The base has an aperture 54 through which the temperature regulation plate extends to contact the gel supporting sheet of a cassette retained within a cassette support 56 in use. The detachable lid has a central window 58 through which a mounted cassette may be viewed, four electrical circuits 60 and an electrical terminal 62 associated with each electrical circuit for connection to an external electrophoresis power supply. Each of the four electrical circuits extends to metal pins around the central window which, when a cassette is located within the cassette support and the lid is closed, extends through a respective access port and bore through the insulating spacer, to connect an individual electrode to the respective electrical circuit.

Figure 6A:
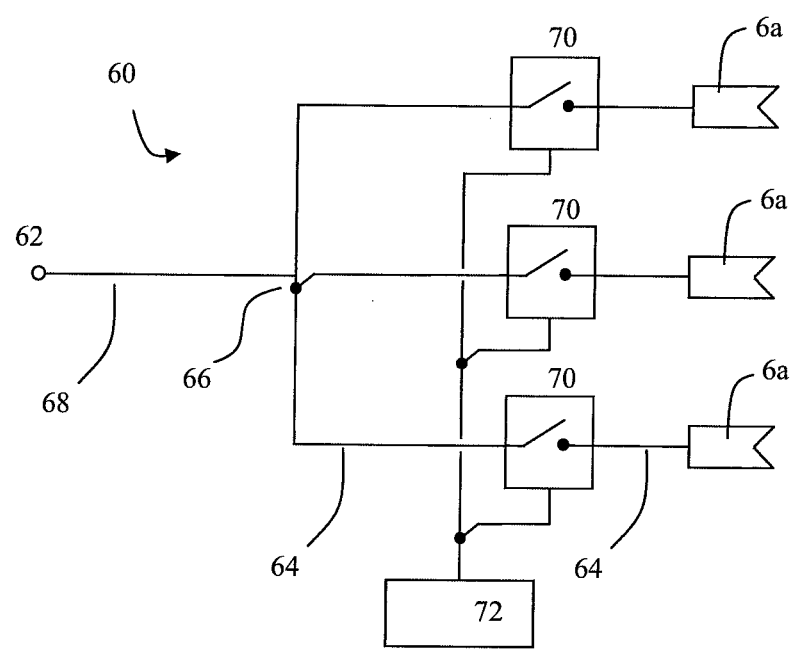
FIG. 6A is an electrical circuit for isolation of one group of discrete electrodes.
Figure 6B:
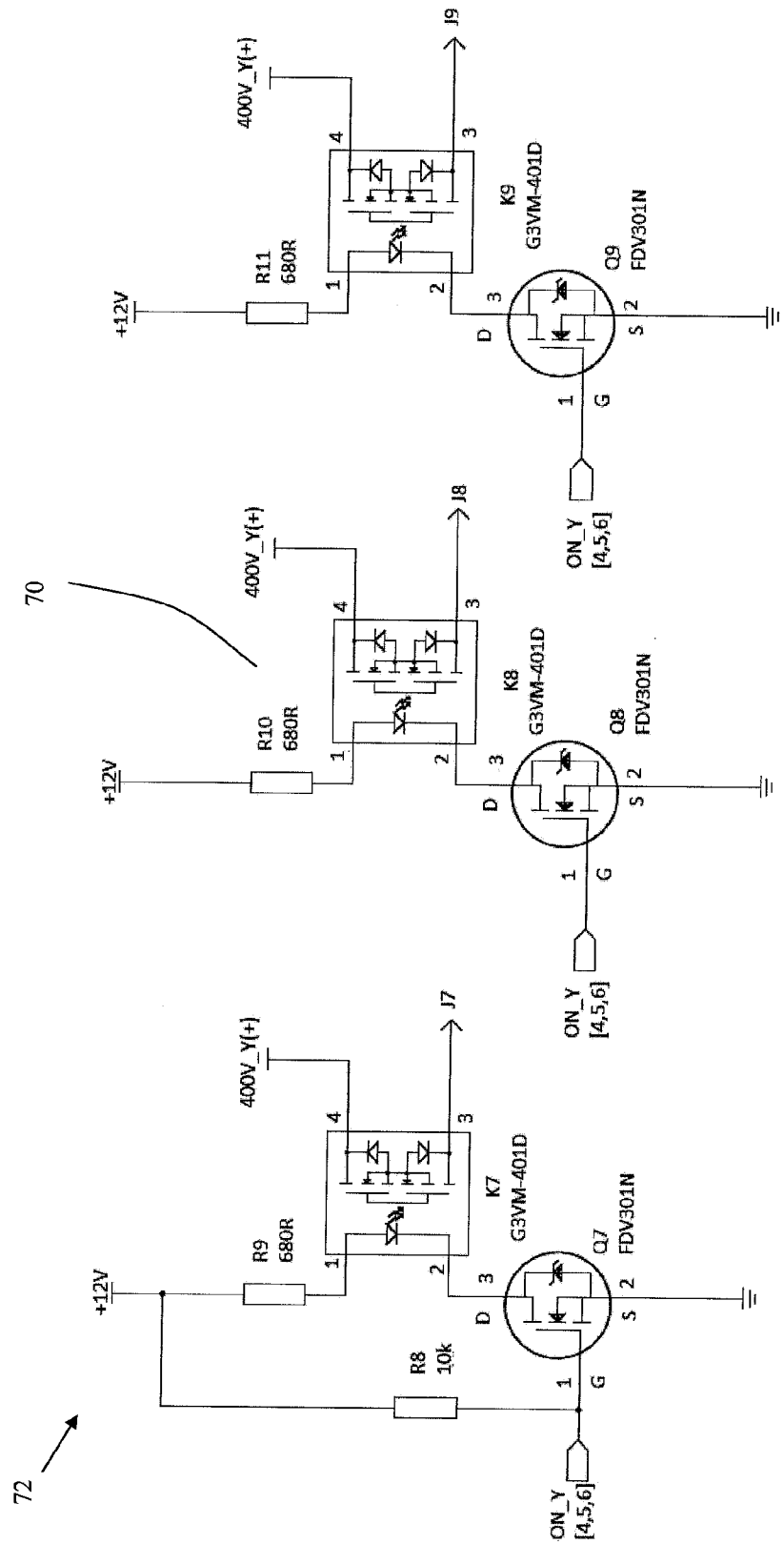
FIG. 6B is an array of relay isolation switches.

When the cassette is mounted within the interface unit in this way, the discrete electrodes within a group of discrete electrodes (6a, 6b, 6c or 6d) are connected by way of an electrical circuit which extends between each electrode within the group and the respective electrical terminal for attachment to a pole of an electrophoresis power supply. Each electrical circuit comprises a wired connection 64 extending from each of the electrodes through the respective metal connecting pin to a junction 66 and a wire 68 extending from the junction to the respective electrical terminal 62. Between each electrode and the junction is located a relay 70 switched by a switch regulator 72. Although FIGS. 6A and 6B illustrate electrical circuits including a separate relay for each electrode, a one or more multi-pole relays, operable to connect or disconnect a plurality of electrodes from the electrical terminal, could be provided for each group of discrete electrodes. Instead of relays, other electronic switches, such as solid state switches, may be employed.

The potential difference applied in use between opposed groups of discrete electrodes may be several hundred volts (for example, 400V), but the potential difference output by the switch regulator typically may be much less, for example 5V, enabling the switch regulator to readily interface with a microprocessor 74 or other controller provided within the control unit and operable to control the electrophoresis process by providing signals to the switch regulators and by controlling other functions, for example, controlling the temperature of the temperature regulation plate.

In use, a cassette comprising polyacrylamide/TBE gel matrix containing urea (a temperature-dependent denaturing agent) is mounted onto the interface unit. When the lid is closed, the metal pins extend into the cassette to contact the electrodes within the cassette.

A user sets the experimental conditions, if required, through a user interface of the control unit. Typically, the user will set a desired temperature, for example 4° C. The control unit causes the temperature regulation plate to regulate the temperature of the cassette to reach the desired temperature. A sample is then introduced into the gel matrix through the sample loading aperture and the user presses a button to indicate that the separation process should begin. In some applications, the sample will be introduced into the gel matrix before the temperature of the gel is set.

Before separation commences, each electrode is electrically isolated from all other electrodes and from the power supply by way of the relays. To commence separation, the controller signals the switch regulators associated with the electrical circuits connected with group of discrete electrodes 6a and opposed group of discrete electrodes 6b to close the respective relays which they regulate. A potential difference supplied by an external electrophoresis power supply is supplied to the electrodes such that each of the electrodes 6a within one group are connected to each other and to one pole of the power supply and each of the electrodes 6b within the other opposing group are connected to each other and to another pole of the power supply, thereby generating an electrical field through the electrophoresis zone in a first direction. Charged molecules within the sample begin to move in the first direction at a rate determined by their net charge, size and conformation.

Whilst electrophoresis occurs in the first direction, the electrodes within the two groups 6c, 6d which form the second set of electrodes, are electrically isolated from each other and from the electrophoresis power supply. As a result, they distort the electrical field generated by the first set of electrodes less than would be the case if a single elongate electrode extended along each of the second pair edges of electrophoresis zone or if the electrodes within each group were in electrical communication with each other.

After a preset period of time, the controller signals the switch regulators to cause the respective relays to isolate each electrode, switching off the potential difference in the electrophoresis zone.

Under the control of the controller, the temperature of the temperature regulation plate is increased, for example to 37° C., and the gel support is incubated at that temperature until the gel matrix within the electrophoresis zone has reached 37° C. At this temperature, urea within the gel matrix denatures nucleic acids with the sample, separating strands of double stranded nucleic acids After a further preset period of time, the controller signals the switch regulators associated with the electrical circuits connected with the group of discrete electrodes 6c and the opposed group of discrete electrodes 6d which together form the second set of electrodes, to close the respective relays which they regulate. A potential difference supplied by an external electrophoresis power supply is supplied to the electrodes such that each of the electrodes 6c within one group are connected to each other and to one pole of the power supply and each of the electrodes 6d within the other opposing group are connected to each other and to another pole of the power supply, thereby generating an electrical field through the electrophoresis zone in a second direction. Charged molecules within the sample begin to move in the second direction at a rate determined by their net charge, size and conformation in their denatured state.

Whilst an electric field is applied in the second direction the electrodes within the two groups of discrete electrodes which form the first set of electrodes are electrically isolated from each other. Again, this arrangement distorts the electrical field generated by the second set of electrodes less than would be the case if a single elongate electrode extended along each of the first pair of edges of the electrophoresis zone or if the electrodes within each group were in electrical communication with each other.

After a preset period of time, the power supply to the temperature regulation plate and the electrodes is cut and the electrophoresis procedure is completed. The gel matrix is removed from the gel support and incubated within a solution or buffer comprising a dye agent operable to label any nucleic acid present within the gel matrix. After labelling the gel matrix is imaged and the image is recorded for analysis.

Figure 7:
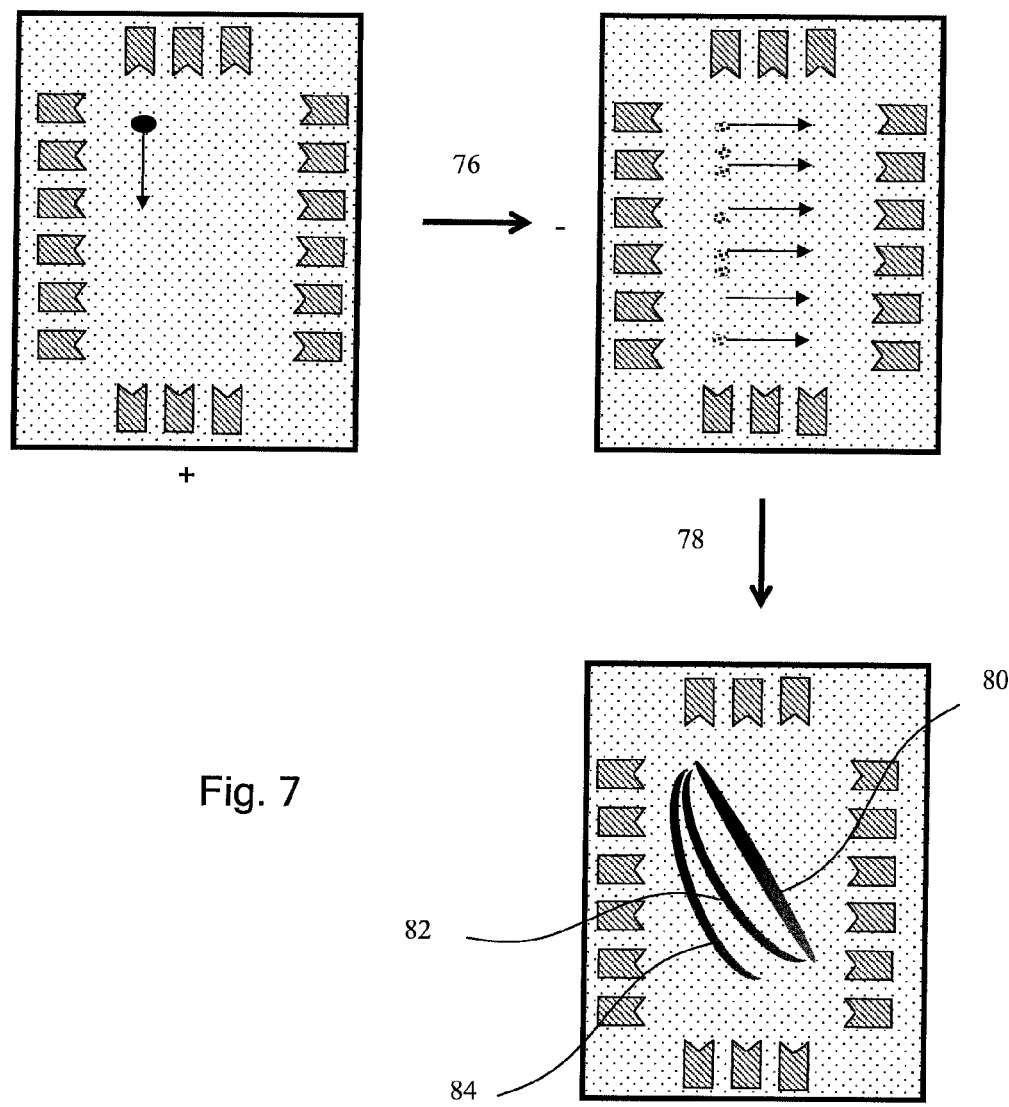
FIG. 7 is a schematic diagram of the separation of a sample of nucleic acid, by the two-dimensional gel electrophoresis process of the present invention.

The effect of the above electrophoresis method is shown in FIG. 7, illustrating a sample of DNA molecules separated in a first direction 76 and then a second direction 78. Single stranded DNA molecules (in the original sample) have been separated, by length, along the diagonal axis 80. Double stranded DNA molecules have been separated, by length, on the curved line 82 beneath the diagonal axis. If the sample were to include RNA-DNA hybrid molecules, they would be separated, by length, on the curved line 84 below both the diagonal axis and the curved line of the double stranded DNA molecules. Thus, a user can rapidly assess the proportion of single stranded DNA and double stranded DNA (or single stranded RNA and double stranded RNA or RNA-DNA hybrids) within the original sample, and the length distribution of molecules of each strandedness.

Another cassette may be introduced into the electrophoresis apparatus and the process repeated to separate molecules within another sample. Due to the high level of automation, the process can be carried out efficiently with minimal user input.

In a typical application, the electrophoresis apparatus is used to separate nucleic acid samples, for example samples of nucleic acids from 100 nucleotides to 2,000 nucleotides in length. However, for samples of molecules of similar size ranges, the degree of separation may be varied by using gel matrices with a higher or lower percentage of polyacrylamide. For example, using a gel matrix with six percent polyacrylamide will allow molecules of a similar mass to migrate further in a given time for a given potential difference than a gel matrix with twelve percent polyacrylamide.

In an alternative embodiment, the automated process controlled by the controller is carried out manually by the user. The voltage applied to a group of discrete electrodes is set by the user and the time the set voltage is applied to the group of discrete electrodes is controlled directly by the user. Whilst such a manual control system is user intensive, it allows the process to dynamically change upon unexpected or unwanted events. For example, the sample may run through the gel in one direction faster than expected and the running time be adjusted accordingly to compensate.

In an alternative embodiment the sample or gel further comprises a fluorescent dye operable to label the nucleic acid molecules present within the sample. In this embodiment the interface unit further comprises a camera operable to image the electrophoresis zone electrophoresis in both the first and second directions. Therefore, it is possible to observe the sample whilst electrophoresis is occurring. In this way it is possible to halt electrophoresis when sufficient molecular separation has occurred, or when the molecules to be separated are in danger of migrating out of the electrophoresis zone.

In an alternative embodiment, the labelled sample within the gel may be imaged during or after electrophoresis using a scanner.

In an alternative embodiment the electrodes defining the first pair of edges of the electrophoresis zone do not extend along the full length of the first pair of edges. For example, a single electrode may be provided on each of the first pair of edges located towards one side of the first pair of edges. This is sufficient for many applications as, during the first electrophoresis step, the sample remains with a linear zone of minimal breadth.

Further variations and modifications may be made within the scope of the invention herein disclosed.

The invention claimed is:

1. A two-dimensional gel electrophoresis apparatus comprising:
   a plurality of electrodes defining an electrophoresis zone; and
   a gel support for retaining an electrophoresis gel in the electrophoresis zone,
   the electrophoresis zone having at least four edges, each of which is defined by at least one of the said plurality of electrodes, the at least four edges comprising first and second pairs of opposed edges, wherein at least one of the second pair of edges is defined by a group of discrete electrodes, some or all of the electrodes having an outer wall with a generally concave formation on the side facing the opposed edge of the electrophoresis zone.

2. The two-dimensional gel electrophoresis apparatus according to claim 1, wherein at least one of:
   both of the second pair of edges are defined by respective groups of discrete electrodes; and
   one or both of the first pair of edges are defined by respective groups of discrete electrodes.

3. Two-dimensional gel electrophoresis apparatus according to claim 1, further comprising isolating means operable in an isolating mode, in which discrete electrodes within a group are isolated, and in an operational mode, in which the discrete electrodes within a group are electrically connected to one or more electrical terminals.

4. The two-dimensional gel electrophoresis apparatus according to claim 3, wherein the isolating means comprises an electrical circuit extending between the electrodes in a group of discrete electrodes and an electrical terminal, the electrical circuit operable between an isolating mode and an operational mode.

5. The two-dimensional gel electrophoresis apparatus according to claim 4, wherein the electrical circuit associated with the group of electrodes determines that at least two of the electrodes within the group of electrodes have different potentials in use.

6. The two-dimensional gel electrophoresis apparatus according to claim 1, comprising a body defining a gel retaining volume therein.

7. The two-dimensional gel electrophoresis apparatus according to claim 1, wherein some or all of the electrodes have an outer wall with a generally concave formation on the side facing the opposed edge of the electrophoresis zone.

8. The two-dimensional gel electrophoresis apparatus according to claim 1, wherein the gel support comprises one or more apertures, each of which is associated with a said electrode, to enable gas produced by the respective electrode to egress from the gel support.

9. The two-dimensional gel electrophoresis apparatus according to claim 8, wherein some or all of the electrodes comprise a gas guiding formation operable to direct generated gas towards a said aperture associated with the respective electrode.

10. The two-dimensional gel electrophoresis apparatus according to claim 1, wherein discrete electrodes in a group of discrete electrodes are arranged in a line defining part of an edge of the electrophoresis zone and wherein the ratio of the discrete electrode width parallel to the respective edge to the sum of said width and the space between discrete electrodes, is between 0.3 and 0.7.

11. The two-dimensional gel electrophoresis apparatus according to claim 1 further comprising electrophoresis gel retained in the electrophoresis zone by the gel support.

12. A method of carrying out two-dimensional gel electrophoresis comprising the steps of:
   providing a plurality of electrodes which define an electrophoresis zone and providing electrophoresis gel in the electrophoresis zone, the electrophoresis zone having at least four edges, each edge defined by at least one of the said plurality of electrodes, the at least four edges comprising first and second pairs of opposed edges, wherein at least one of the second pair of edges is defined by a group of discrete electrodes and some or all of the electrodes have an outer wall with a generally concave formation on the side facing the opposed edge of the electrophoresis zone; and
   applying a potential difference between the electrodes defining the first pair of opposed edges, to generate an electrical field in a first direction across the electrophoresis zone, whilst the electrodes within the or each group of discrete electrodes which define the at least one of the second pair of edges are electrically isolated from each other.

13. A method according to claim 12, wherein both of the second pair of edges are defined by respective groups of discrete electrodes and a potential difference is applied between the group of discrete electrodes which defines one of the first pair of opposed edges and the group of discrete electrodes which define the other of the first pair of opposed edges to generate an electrical field in a first direction across the electrophoresis zone, whilst the electrodes within the or each group of discrete electrodes which define the at least one of the second pair of edges are electrically isolated from each other, and wherein one or both of the first pair of edges are defined by respective groups of discrete electrodes, and wherein the method comprises the step of applying a potential difference between the electrodes defining the second pair of opposed edges to generate an electrical field in a second direction across the electrophoresis zone, whilst the electrodes within the or each group of discrete electrodes which define the at least one of the first pair of edges are electrically isolated from each other.

14. A method according to claim 12, wherein an electrical circuit extends between the electrodes in a group and an electrical terminal, and the method comprises operating the electrical circuit between an isolating mode, where the electrodes in the group are electrically isolated from each other, and an operational mode, in which the electrodes in the group are electrically connected to each other and to the electrical terminal and/or are each electrically connected to the electrical terminal.

15. A method according to claim 12, wherein gas generated at some or all of the electrodes during use egresses from the gel support through an aperture associated with each respective electrode.

16. A method according to claim 12, wherein the electrophoresis gel comprises an activatable denaturing agent and the method comprises the step of activating the activatable denaturing agent after carrying out electrophoresis in a first direction and before carrying out electrophoresis in a second direction.

17. A method according to claim 16, comprising separating a mixture of single stranded and double stranded nucleic acids, or a mixture of proteins.

\* \* \* \* \*